United States Patent [19]

Ducep et al.

[11] 4,185,111
[45] Jan. 22, 1980

[54] DAUNORUBICIN DERIVATIVES

[75] Inventors: Jean-Bernard Ducep, Paris; Daniel Farge, Thiais; Gerard Ponsinet, Sucy en Brie; Daniel Reisdorf, Thiais, all of France

[73] Assignee: Rhone-Poulenc Industries, Paris, France

[21] Appl. No.: 923,448

[22] Filed: Jul. 10, 1978

[30] Foreign Application Priority Data

Jul. 11, 1977 [FR] France .................. 77 21272

[51] Int. Cl.² ............... A61K 31/35; C07D 309/02
[52] U.S. Cl. ....................... 424/283; 260/345.9 R
[58] Field of Search ............... 260/345.9 R; 424/283

[56] References Cited

U.S. PATENT DOCUMENTS 4,012,448  3/1977  Smith et al. .............. 260/345.9 R

*Primary Examiner*—Nicky Chan
*Attorney, Agent, or Firm*—Stevens, Davis, Miller & Mosher

[57] ABSTRACT

Daunorubicin derivatives of the general formula:

wherein each of the symbols R represents a hydrogen atom or a methyl or ethyl radical, are new therapeutically useful compounds possessing anti-tumoral properties.

7 Claims, No Drawings

DAUNORUBICIN DERIVATIVES

The present invention provides, as new compounds, daunorubicin derivatives of the general formula:

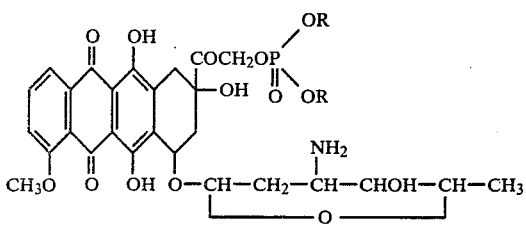

wherein each of the symbols R represents a hydrogen atom or a methyl or ethyl radical, and acid addition salts, preferably hydrochlorides, thereof.

According to a feature of the invention, the daunorubicin derivatives of general formula I wherein R is as hereinbefore defined, or acid addition salts therof, are prepared by reacting a quaternary ammonium phosphate of the general formula:

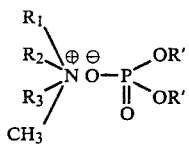

wherein each of the symbols R' represents a hydrogen atom, a methyl or ethyl radical, or a protective radical, and the symbols $R_1$, $R_2$ and $R_3$, which are the same or different, represent alkyl radicals containing 1 to 4 carbon atoms, with 14-bromodaunorubicin of the formula:

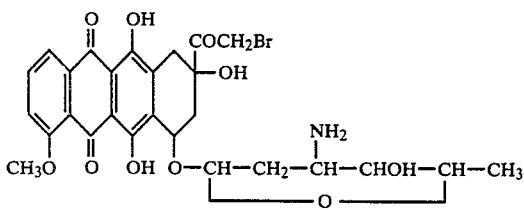

, or an acid addition salt thereof, after which, when R' represents a protective radical, removing by methods known per se the protective radical in order to obtain a compound of general formula I in which at least one of the radicals R is a hydrogen atom, or an acid addition salt thereof.

The reaction between the compounds of general formulae II and III is generally carried out in an organic solvent such as a ketone (e.g. acetone), a nitrile (e.g. acetonitrile) or an amide (e.g. dimethylformamide), at a temperature between 20° and 60° C. The 14-bromodaunorubicin is preferably reacted in the form of the hydrochloride with a tetramethylammonium phosphate conforming to general formula II.

When R' in the reactant of general formula II is a protective radical, the tert.-butyl radical is preferably used. The protective radical is generally removed by the action of hydrochloric acid and the reaction is carried out in a chlorine-containing solvent (e.g. methylene chloride) or in acetonitrile, at a temperature between 0° and 20° C. It is not obligatory to purify the product obtained before removing the protective radical.

The compounds of general formula II can be prepared in accordance with the process described by R. Hazard et al., C. R. Acad. Sci., 244, 1556 (1957), by P. Chabrier et al., C. R. Acad. Sci., 244, 2730 (1957), by J. Cheymol et al., C. R. Acad. Sci., 247, 1014 (1958) or by A. Zwierzak et al., Tetrahedron, 27, 3163 (1971).

14-Bromodaunorubicin of formula III and its preparation have been described in French Patent Application No. FR 2331151.

The daunorubicin derivatives of general formula I obtained by the aforedescribed process can optionally be purified by physical methods such as crystallisation or chromatography, or by chemical methods such as the formation of acid addition salts, crystallisation of the salts and decomposition of them in an alkaline medium.

The daunorubicin derivatives of general formula I can be converted by methods known per se into acid addition salts, for example by reaction of the basic compounds with acids in appropriate solvents, for example alcohols, ethers, ketones or chlorinated hydrocarbons. The salt which is formed is precipitated if necessary after concentration of its solution, and is isolated by filtration or decantation.

By the term "methods known per se" as used in this specification is meant methods heretofore used or described in the chemical literature.

The new daunorubicin derivatives of the general formula I, and their acid addition salts, possess valuable anti-tumoral properties coupled with a low toxicity.

They have proved particularly active against graftable tumours in mice at doses of between 0.25 and 10 mg/kg animal body weight, administered intraperitoneally, against leukaemia L 1210, and at doses of 4 to 20 mg/kg animal body weight, administered intravenously, against pulmonary carcinoma.

Their maximum tolerated dose has been determined on mice. It is between 1 and 10 mg/kg animal body weight administered intraperitoneally.

For therapeutic purposes the daunorubicin derivatives of general formula I may be employed as such or in the form of non-toxic acid addition salts, i.e. salts containing anions which are relatively innocuous to the animal organism in therapeutic doses of the salts (such as hydrochlorides, sulphates, nitrates, phosphates, acetates, propionates, succinates, benzoates, fumarates, maleates, tartrates, theophyllineacetates, salicylates, phenolphthalinates and methylene-bis-β-hydroxynaphthoates) so that the beneficial physiological properties inherent in the bases are not vitiated by side-effects ascribable to the anions.

The following Examples illustrate the preparation of daunorubicin derivatives of general formula I by the process hereinbefore described for their preparation.

EXAMPLE 1

A mixture of 14-bromodaunorubicin hydrochloride (5 g) and tetramethylammonium dimethylphosphate (7.8 g) in acetone (2000 cc) is stirred for 20 hours in an anhydrous atmosphere. The suspension is then heated under reflux for 90 minutes. After cooling, the precipitate formed is filtered off and washed with chloroform (300 cc). The filtrate is concentrated to dryness under reduced pressure (20 mm Hg). The residue is chromatographed on silica (150 g). Elution is carried out first with chloroform (500 cc) in order to remove the impurities of low polarity, and then with a mixture (about 2 liters) of ethyl acetate and methanol (1-1 by volume). After evaporating the solvents from the second eluate under reduced pressure (20 mm Hg) at a temperature which does not exceed 30° C., a solid product (6.5 g) is isolated. This product is dissolved in chloroform (400 cc) and the organic phase thus obtained is washed with an ice-cooled, saturated solution of sodium bicarbonate (200 cc) and then with water (400 cc). The organic phase is dried over sodium sulphate. After filtration and concentration to dryness under reduced pressure (20 mm Hg) at a temperature below 30° C., the solid obtained is dissolved in chloroform (175 cc) and a 0.465N solution (7.8 cc) of anhydrous hydrogen chloride in dioxan is added at about 0° C., whilst stirring. The precipitation is completed by adding ethyl acetate (175 cc).

After 30 minutes, the precipitate is filtered off. After drying, 14-dimethoxyphosphoryloxydaunorubicin hydrochloride (2.43 g) is thus obtained in the form of a red powder.

Rf=0.38 [silica gel; methylene chloridemethanol-formic acid-water (88-15-2-1 by volume)].

Analysis %, calculated: C, 50.63; H, 5.13; Cl, 5.15; N, 2.04; P, 4.50. found: C, 51.8; H, 6.1; Cl, 3.8; N, 1.9; P, 3.7.

EXAMPLE 2

A mixture of 14-bromodaunorubicin hydrochloride (15.8 g) and tetramethylammonium diethylphosphate (12.25 g) in dimethylformamide (1 liter) is stirred for 20 hours at 20° C. and in an anhydrous atmosphere. An insoluble material is filtered off and washed with chloroform (3×30 cc), and the filtrate and the chloroform phases are then concentrated to dryness under reduced pressure (1 mm Hg) without exceeding 40° C.

The evaporation residue is taken up in chloroform (250 cc) and an insoluble material is filtered off. The filtrate is concentrated to dryness under reduced pressure (20 mm Hg) at 30° C. The pasty residue is taken up in a mixture (700 cc) of chloroform and ethyl acetate (1-1 by volume) and extraction is then carried out with 0.2N hydrochloric acid (4×400 cc). The acid solutions are washed with ethyl acetate (4×700 cc) and then extracted with butanol (2×1500 cc). The butanol extract is concentrated to dryness under reduced pressure (1 mm Hg) without exceeding 40° C. The solid thus obtained is dissolved in chloroform (300 cc); the solution is dried, filtered and evaporated under reduced pressure (20 mm Hg) at 40° C. The evaporation residue is taken up in ethyl acetate (1 liter) and the insoluble material is filtered off and washed with diethyl ether. After drying, 14-diethoxyphosphoryloxydaunorubicin hydrochloride (7 g) is obtained having the following characteristics:

Rf: 0.30 [silica gel; methylene chloridemethanol-formic acid-water (88-15-2-1 by volume)]

Analysis %; calculated: C, 52.00; H, 5.49; Cl, 4.95; N, 1.96; P, 4.32. found: C, 51.7; H, 5.9; Cl, 5.3; N, 2.1; P, 4.8.

Tetramethylammonium diethylphosphate can be prepared in accordance with the process described by P. Chabrier et al., C. R. Acad. Sci., 244, 2730 (1957).

EXAMPLE 3

A mixture of 14-bromodaunorubicin hydrochloride (6.43 g) and tetramethylammonium methyl-ethyl-phosphate (10.6 g) in dimethylformamide (200 cc) is stirred for 80 hours at 20° C.

The mixture is then concentrated to dryness under reduced pressure (1 mm Hg) without exceeding 40° C. The residue is taken up in chloroform (100 cc), the insoluble material is filtered off and the filtrate is concentrated to dryness under reduced pressure (20 mm Hg) at 20° C. The solid obtained is dissolved in methylene chloride (2 liters) and the solution is filtered through silica gel (250 g). After evaporating off the solvent under reduced pressure (20 mm Hg) at 20° C., an amorphous red solid (3.1 g) is isolated.

This solid is dissolved in chloroform (50 cc); the solution is cooled in a bath of ice-cooled water and a 0.77N solution (4.54 cc) of anhydrous hydrogen chloride in dioxan is added, whilst stirring. A precipitate forms. The mixture is stirred for 1 hour 30 minutes at 20° C. and ethyl acetate (300 cc) is then added. The precipitate is filtered off, washed with ethyl acetate (3×50 cc) and then diethyl ether (3×75 cc). After drying, 14-ethoxy-methoxy-phosphoryloxydaunorubicin hydrochloride (1.9 g) is obtained in the form of a red powder.

Rf; 0.35 [silica gel; methylene chloridemethanol-formic acid-water (88-15-2-1 by volume)]

Analysis %, calculated: C, 51.33; H, 5.31; Cl, 5.05; N, 2.00; P, 4.41. found: C, 49.6; H, 5.7; Cl, 6.2; N, 2.1; P, 3.9.

The tetramethylammonium salt of ethylmethylphosphoric acid can be prepared in accordance with the process described by J. Cheymol et al., C. R. Acad. Sci., 247, 1014 (1958).

EXAMPLE 4

A mixture of 14-bromodaunorubicin hydrochloride (6.42 g) and tetramethylammonium di-tert.-butylphosphate (5.66 g) in dimethylformamide (400 cc) is stirred for 2 hours 30 minutes at a temperature of about 20° C. in an anhydrous atmosphere.

The mixture is then concentrated to dryness under reduced pressure (1 mm Hg) without exceeding 40° C. The residue is taken up in diethyl ether (1200 cc), and the insoluble product is filtered off and dried under reduced pressure (1 mm Hg). The solid thus obtained is chromatographed on silica gel (200 g), elution being carried out first with methylene chloride (2 liters) and then with a mixture (1.5 liters) of methylene chloride and methanol (8-2 by volume). The second eluate is concentrated to dryness under reduced pressure (20 mm Hg) at a temperature of about 30° C. An amorphous powder (3.9 g) is thus isolated. This powder (3 g) is dissolved in methylene chloride (200 cc). The solution is cooled in a bath of ice-cooled water and a 0.77N solution (15.6 cc) of anhydrous hydrogen chloride in dioxan is added slowly. The mixture is stirred for 1 hour at about 5° C. and then for 2 hours at 20° C. A precipitate forms during this period. Methylene chloride (300 cc) is added to the suspension and the precipitate is then filtered off. The solid is washed with methylene chloride (4×100 cc) and then with diethyl ether (4×100 cc). After drying, 14-dihydroxyphosphoryloxydaunorubicin hydrochloride (1.6 g) is obtained in the form of a red powder.

Analysis %; calculated: C, 49.14; H, 4.74; N, 2.12; P, 4.69. found: C, 48.8; H, 5.5; N, 2.4; P, 4.2.

Tetramethylammonium di-tert.-butylphosphate can be prepared in accordance with the process described by A. Zwierzak et al., Tetrahedron, 27, 3163 (1971).

The present invention includes within its scope pharmaceutical compositions which comprise, as active ingredient, at least one daunorubicin derivative of general formula I, or a non-toxic acid addition salt thereof, in association with a compatible pharmaceutical carrier, which may be inert or physiologically active. The compositions may be in any of the forms appropriate for the envisaged method of administration. Parenteral administration, especially intravenous administration, is the preferred method.

The compositions according to the invention for parenteral administration include sterile aqueous or non-aqueous solutions, suspensions or emulsions. Examples of non-aqueous solvents or vehicles are propylene glycol, polyethylene glycol, vegetable oils such as olive oil and injectable organic esters such as ethyl oleate. These compositions can also contain adjuvants such as preserving, wetting, emulsifying and dispersing agents. They may be sterilized by, for example, filtration through a bacteria-retaining filter, by incorporation in the compositions of sterilizing agents or by irradiation. They may also be manufactured in the form of sterile solid compositions which can be dissolved or dispersed, at the time of use, in sterile water or any other injectable sterile medium.

The daunorubicin derivatives of general formula I and their non-toxic acid addition salts are, more particularly, useful in the treatment of acute lymphoblastic and myeloblastic leukaemias and solid tumours at doses which are generally between 1 and 5 mg/kg body weight per day, administered intravenously, in the case of an adult.

The following Example illustrates pharmaceutical compositions according to the invention.

EXAMPLE 5

A solution containing 14-dimethoxyphosphoryloxydaunorubicin hydrochloride (28.27 mg/cc) is prepared by dissolving this product (4.24 g) in an apyrogenic physiological solvent in an amount sufficient to obtain 150 cc. The solution obtained is divided, under aseptic conditions, into ampoules, in an amount of 3 cc per ampoule. The ampoules are sealed and each contains 80 mg of 14-dimethoxyphosphoryloxydaunorubicin (base).

We claim:
1. A daunorubicin derivative of the formula:

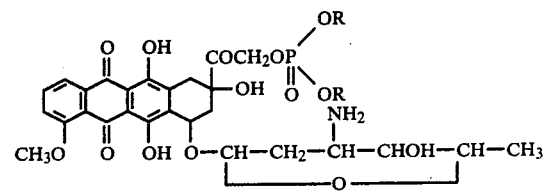

wherein each of the symbols R represents a hydrogen atom or a methyl or ethyl radical, and its non-toxic acid addition salts.

2. A daunorubicin derivative according to claim 1 which is 14-dimethoxyphosphoryloxydaunorubicin, and its non-toxic acid addition salts.

3. A daunorubicin derivative according to claim 1 which is 14-diethoxyphosphoryloxydaunorubicin, and its non-toxic acid addition salts.

4. A daunorubicin derivative according to claim 1 which is 14-ethoxy-methoxy-phosphoryloxydaunorubicin, and its non-toxic acid addition salts.

5. A daunorubicin derivative according to claim 1 which is 14-dihydroxyphosphoryloxydaunorubicin, and its non-toxic acid addition salts.

6. The hydrochloride of a daunorubicin derivative as claimed in claim 1.

7. A pharmaceutical composition useful in the treatment of acute lymphoblastic and myeloblastic leukaemias and solid tumours which comprises, as active ingredient, an effective amount of a daunorubicin derivative as claimed in claim 1, or a non-toxic acid addition salt thereof, in association with a compatible pharmaceutically acceptable carrier.

* * * * *